US008614278B2

(12) United States Patent
Loubert et al.

(10) Patent No.: US 8,614,278 B2
(45) Date of Patent: Dec. 24, 2013

(54) SILICONE ACRYLATE HYBRID COMPOSITION AND METHOD OF MAKING SAME

(75) Inventors: Gary Lee Loubert, Saginaw, MI (US); Tiffany Anne Menjoulet, Clare, MI (US); Timothy Paul Mitchell, Clio, MI (US); Xavier Jean-Paul Thomas, Famars (FR)

(73) Assignees: Dow Corning Corporation, Midland, MI (US); Dow Corning France SAS, Lyons Cedex (FR)

( * ) Notice: Subject to any disclaimer, the term of this patent is extended or adjusted under 35 U.S.C. 154(b) by 0 days.

(21) Appl. No.: 13/306,467

(22) Filed: Nov. 29, 2011

(65) Prior Publication Data

US 2012/0114737 A1  May 10, 2012

Related U.S. Application Data

(63) Continuation-in-part of application No. 12/303,362, filed as application No. PCT/US2007/013321 on Jun. 6, 2007, now Pat. No. 8,124,689.

(60) Provisional application No. 60/811,246, filed on Jun. 6, 2006.

(51) Int. Cl.
C08L 83/07 (2006.01)
A61K 9/70 (2006.01)

(52) U.S. Cl.
USPC ........... 525/100; 424/443; 424/447; 424/448; 525/105; 525/477; 526/279; 526/319; 526/325; 526/328; 528/24; 528/32

(58) Field of Classification Search
None
See application file for complete search history.

(56) References Cited

U.S. PATENT DOCUMENTS

| | | | |
|---|---|---|---|
| 2,490,357 A | 12/1949 | Hyde | |
| 2,542,334 A | 2/1951 | Hyde | |
| 2,736,721 A | 2/1956 | Dexter | |
| 2,814,601 A | 11/1957 | Currie et al. | |
| 2,857,356 A | 10/1958 | Goodwin, Jr. | |
| 2,927,907 A | 3/1960 | Polmanteer | |
| RE24,906 E | 12/1960 | Ulrich | |
| 3,002,951 A | 10/1961 | Johannson | |
| 3,161,644 A | 12/1964 | Janssen | |
| 3,186,967 A | 6/1965 | Nitzsche et al. | |
| 3,509,191 A | 4/1970 | Atwel | |
| 3,528,940 A | 9/1970 | Modie | |
| 3,697,473 A | 10/1972 | Polmanteer et al. | |
| 3,731,683 A | 5/1973 | Zaffaroni | |
| 3,797,494 A | 3/1974 | Zaffaroni | |
| 4,031,894 A | 6/1977 | Urquhart et al. | |
| 4,336,243 A | 6/1982 | Sanvordeker et al. | |
| 4,618,644 A | 10/1986 | Liu | |
| 4,655,767 A | 4/1987 | Woodard et al. | |
| 4,791,163 A | 12/1988 | Traver et al. | |
| 5,063,254 A | 11/1991 | Nakos | |
| 5,308,887 A | 5/1994 | Ko et al. | |
| 5,418,016 A | 5/1995 | Cornforth et al. | |
| 5,464,659 A | 11/1995 | Melancon et al. | |
| 5,474,783 A | 12/1995 | Miranda et al. | |
| 5,624,763 A | 4/1997 | Melancon et al. | |
| 5,656,286 A | 8/1997 | Miranda et al. | |
| 5,965,154 A * | 10/1999 | Haralambopoulos | 424/449 |
| 5,982,041 A * | 11/1999 | Mitani et al. | 257/783 |
| 6,024,976 A | 2/2000 | Miranda et al. | |
| 6,221,383 B1 | 4/2001 | Miranda et al. | |
| 6,235,306 B1 | 5/2001 | Miranda et al. | |
| 6,337,086 B1 | 1/2002 | Kanios et al. | |
| 6,387,487 B1 | 5/2002 | Greenberg et al. | |
| 6,465,004 B1 | 10/2002 | Rossi-Montero et al. | |
| 6,638,528 B1 | 10/2003 | Kanios | |
| 8,124,689 B2 | 2/2012 | Loubert et al. | |
| 2002/0168401 A1* | 11/2002 | Kanios et al. | 424/449 |
| 2006/0034905 A1* | 2/2006 | Singh et al. | 424/449 |
| 2008/0300358 A1 | 12/2008 | Cook et al. | |
| 2009/0048124 A1 | 2/2009 | Leamon et al. | |
| 2009/0196911 A1 | 8/2009 | Loubert et al. | |
| 2012/0108560 A1 | 5/2012 | Evans et al. | |

FOREIGN PATENT DOCUMENTS

| | | |
|---|---|---|
| EP | 0278618 A2 | 8/1988 |
| EP | 289929 A2 | 11/1988 |
| EP | 0429222 A1 | 5/1991 |
| EP | 1002846 A1 | 5/2000 |
| EP | 1025843 A2 | 8/2000 |
| EP | 1076081 A1 | 2/2001 |
| JP | 62295982 A | 12/1987 |
| JP | 63291971 A | 11/1988 |
| WO | WO 9216591 A1 | 10/1992 |
| WO | WO 9216593 A2 | 10/1992 |

(Continued)

OTHER PUBLICATIONS

English language abstract for JP 62295982 extracted from espacenet.com database, dated Apr. 28, 2009.
English language abstract for JP 63291971 extracted from espacenet.com database, dated Jun. 23, 2009.
PCT International Search Report for PCT/US2007/013321 dated May 7, 2008, 9 pages.
Article: Chien et al., "Novel Drug Delivery System—Drugs and the Pharmaceutical Sciences", 1982, vol. 14, pp. 149-217.

(Continued)

Primary Examiner — Marc Zimmer
(74) Attorney, Agent, or Firm — Howard & Howard Attorneys PLLC

(57) ABSTRACT

A silicone acrylate hybrid composition includes the reaction product of a silicon-containing pressure sensitive adhesive composition, an ethylenically unsaturated monomer, and an initiator. The silicon-containing pressure sensitive adhesive composition includes acrylate or methacrylate functionality. A method of making the hybrid composition includes polymerizing the ethylenically unsaturated monomer and the silicon-containing pressure sensitive adhesive composition in the presence of the initiator.

23 Claims, No Drawings

(56) References Cited

FOREIGN PATENT DOCUMENTS

| | | |
|---|---|---|
| WO | WO 9220751 A1 | 11/1992 |
| WO | WO 9220752 A1 | 11/1992 |
| WO | WO 9639458 A1 | 12/1996 |
| WO | WO 02077287 A1 | 10/2002 |
| WO | WO 2007050580 A2 | 5/2007 |
| WO | WO 2007/145996 A2 | 12/2007 |
| WO | WO 2010/124187 A2 | 10/2010 |

OTHER PUBLICATIONS

Article: Bartell, "Chapter 19—Saturated Paper and Saturated Paper Tapes", Handbook of Pressure-Sensitive Adhesive Technology, 1982, pp. 404-418.
Article: Fukuzawa et al. "Chapter 21—Packaging Tapes", Handbook of Pressure-Sensitive Adhesive Technology, 1982, pp. 426-437.
Article: Odian, Principles of Polymerization, Wiley-Interscience, 4th Edition, 2004, pp. 198-332.
Article: Auchter et al., "Chapter 19—Acrylic Adhesives", Handbook of Pressure-Sensitive Adhesive Technology, 1999, pp. 444-514.
Article: Jones, "Chapter 21—Silicone Pressure Sensitive Adhesives", Handbook of Pressure-Sensitive Adhesive Technology, 1999, pp. 550-559.
European Search Report for Application No. EP 12 18 9221 dated Jan. 16, 2013, 2 pages.
European Search Report for Application No. EP 12 19 4816 completed on Mar. 12, 2013; 2 pages.

* cited by examiner

US 8,614,278 B2

SILICONE ACRYLATE HYBRID COMPOSITION AND METHOD OF MAKING SAME

RELATED APPLICATIONS

This application is a continuation of U.S. Non-Provisional application Ser. No. 12/303,362, filed on Dec. 3, 2008, which claims priority to and all the advantages of International Patent Application No. PCT/US2007/013321, filed on Jun. 6, 2007, which claims priority to U.S. Provisional Patent Application No. 60/811,246 filed on Jun. 6, 2006, each of which is expressly incorporated herein by reference in its entirety.

FIELD OF THE INVENTION

The present invention generally relates to a silicone acrylate hybrid composition and a method of making the hybrid composition. More specifically, the present invention relates to a silicone acrylate hybrid composition that is the reaction product of a silicon-containing pressure sensitive adhesive composition comprising acrylate or methacrylate functionality, an ethylenically unsaturated monomer, and an initiator. In the method, the ethylenically unsaturated monomer and the silicon-containing pressure sensitive adhesive composition are polymerized in the presence of the initiator.

BACKGROUND OF THE INVENTION

Pressure sensitive adhesives, also referred to as "PSAs", are known in the art and are commercially available. Some of the more common types of PSAs are formulations based on acrylates, polyurethanes, natural rubbers, synthetic rubbers, and silicones. These PSAs are typically formulated for end use and find utility in a wide variety of applications including tapes, labels, bandages, transdermal drug delivery systems (e.g. patches), laminating adhesives, and transfer adhesives.

Acrylate-based PSAs, also referred to throughout as acrylate PSAs, are broadly used in these applications due to the fact that they are relatively low in cost when compared to other PSAs, solubilize many types of functional drugs for transdermal patches, adhere well to a variety of different surfaces, and can be formulated to build adhesion to a surface, if necessary. The disadvantages of acrylate-based PSAs include poor high temperature performance, poor low temperature performance, inability to adhere to surfaces with low surface energies, and the potential to build excessive adhesion to the skin in medical tape applications which can result in painful removal for the user. Examples of such acrylate-based PSAs are disclosed in U.S. Pat. No. RE 24,906.

Silicone-based PSAs, also referred to throughout as silicone PSAs, are typically produced by either blending or condensing together a silicone resin and a silicone polymer, such as polydimethylsiloxane (PDMS). Silicone materials by nature are very stable at high temperatures and the low glass transition temperature (Tg) of PDMS (less than −115° C.) ultimately provides a PSA that can find use in temperatures ranging from −100° C. to 265° C. Silicone-based PSAs also have excellent chemical inertness, electrical insulating properties, biocompatibility, and the ability to adhere to low surface energy substrates such as silicone release liners, polytetrafluoroethylene, and fluorohalocarbon materials. The primary disadvantage of silicone-based PSAs is their high cost compared to other technologies. Other limitations include lower tack and limited adhesion build (when necessary) in comparison to acrylate-based PSAs. Examples of such silicone-based PSAs are disclosed in U.S. Pat. Nos. 2,736,721; 2,814,601; 2,857,356; and 3,528,940.

There have been many attempts to combine acrylate PSAs and silicone PSAs to gain the advantages of both technologies. As a more specific example of one particular application, silicone pressure sensitive adhesives are frequently applied in the transdermal drug delivery systems. As is known, these systems typically include an active agent and the silicone pressure sensitive adhesive. The active agent, for example a pharmaceutical drug, is for controlled transdermal delivery or release to a substrate, such as the skin of a user of the system. The pressure sensitive adhesive functions to maintain contact between the system and the substrate for extended periods of time such that the active agent can be delivered to the substrate. Examples of such systems can be found in U.S. Pat. Nos. 3,731,683; 3,797,494; 4,031,894; and 4,336,243. Due to the particular silicone pressure sensitive adhesives used, the transdermal drug delivery systems of this prior art do not sufficiently optimize the solubility of the active agent in the pressure sensitive adhesives. As a result, the rate at which the active agent is released from the system for delivery to the substrate and also the total amount of the active agent that is ultimately released and delivered to the substrate are not optimized in this prior art.

In U.S. Pat. Nos. 5,474,783; 5,656,286; 6,024,976; 6,221,383; 6,235,306; 6,465,004; and 6,638,528, all to Noven Pharmaceuticals, Inc., the solubility of an active agent in a transdermal drug delivery system is optimized by simply blending acrylate pressure sensitive adhesives and silicone pressure sensitive adhesives together in varying ratios. However, because the two, separate PSAs are not actually chemically reacted together, domains of one PSA form within the continuous phase of the other PSA. In essence, gross phase separation occurs between the silicone-based PSA and the acrylate-based PSA upon drying. As is known in the art, phase separation is generally caused by the incompatibility of two dissimilar materials, such as in the simple example of oil and water. In this particular case, the lower surface energy of the silicone PSA becomes incompatible with the higher surface energy of the acrylate PSA and phase separation occurs. Phase separation is also commonly referred to as instability. This instability limits the effective use time of the acrylate pressure sensitive adhesive/silicone pressure sensitive adhesive blend prior to and during application before phase separation occurs. Also, upon drying and as the blend ages over time, the size of the domains can potentially change as the two distinct PSAs try to reach an equilibrium state. This can lead to changes in properties such as tack, skin adhesion, and release from liner with time.

In another example, JP 62-295982, to Toyoda Gosei Co. LTD, describes a mounting system for an automotive application that consists of a molding and a PSA made by combining a silicone-based PSA, an acrylate-based PSA, and a polyurethane and/or polyisocyanate crosslinker together. The purpose of this mounting system is to provide a composition to mount a molding to an automobile main frame. For the silicone-based PSA and the acrylate-based PSA to be put together, a third polymeric species, specifically the polyurethane and/or polyisocyanate crosslinker, must be used to react the separate phases together. The disadvantages of this system include the requirement for the third polymeric species, a limited formulated pot life due to immediate reaction of the crosslinker, and unstable shelf-life stability of the coated product as the system will continue to crosslink with age, i.e., over time.

U.S. Pat. No. 4,791,163 to General Electric Company describes an emulsion that comprises (a) 100 parts by weight of water; (b) 10 to 400 parts by weight of PSA comprising: (i) from about 50 to 99% by weight of an organic PSA; (ii) from 1 to about 50% by weight of a silicone PSA; and (c) an effective amount of emulsifying agent to maintain the emulsion. The silicone-based PSA in solvent is first emulsified and then subsequently added to the organic PSA to provide the final composition. In this example, it is necessary to have careful control of the emulsifying agent and drying conditions to prevent premature phase separation of the emulsion prior to and during the drying step. Once the emulsion has been dried, there is no actual chemical reaction that occurs between the silicone PSA and the organic PSA.

Another example, EP 0 289 929 B1 also to the General Electric Company, describes the same emulsion as in the '163 patent with the addition of an effective amount of organic peroxide or alkoxy silane crosslinking agent to increase the shear strength of the emulsion through crosslinking within the silicone phase. Again, the emulsion requires the careful control of the emulsifying agent to prevent gross phase separation of the emulsion prior to and during the drying step.

In another example, JP 63-291971, to Nitto Electric Ind. Co. LTD, describes an adhesive that comprises a mixture of a silicone PSA, an acrylate PSA, and a silicone-acrylic graft copolymer. The silicone-acrylic graft copolymer is formed by the reaction of a silicone macromonomer with acrylic monomers during a polymerization reaction. The silicone-acrylic graft copolymer is then added to a blend of silicone PSA and acrylic PSA composition to act as a compatibiliser between the two different PSA phases. Because there is no actual chemical reaction between the PSAs, there still remains the potential for phase separation.

In WO 92/20751 to Minnesota Mining and Manufacturing Company (3M), a pressure sensitive adhesive composition typically consists of acrylic monomer, a silicone pressure-sensitive adhesive, optional photoinitiator and optional crosslinker. Another series of 3M patents relating to vibration damping disclose this same composition (see WO 92/20752, and U.S. Pat. Nos. 5,464,6659 and 5,624,763). The goal of these compositions is to provide a solventless, radiation curable composition for use in PSA or vibration damping applications. The commercially available silicone PSA is first dried of all solvent. The solid silicone PSA mass is then dissolved in the desired monomer(s) followed by the addition of the photoinitiator and the crosslinker. The composition is then coated onto a substrate and cured into a final product by exposure to UV radiation. Although a crosslinker can be added, the composition is essentially an interpenetrating network where the acrylic monomer reacts while dispersed within the preformed silicone PSA network. The advantages of this composition are the ability to control the silicone PSA to acrylate ratio and also the ratio of acrylate monomer(s) within the acrylate itself depending on final use properties. As is clearly stated throughout these patents, the components of the composition are selected such that when the silicone PSA has been dispersed into the monomers to form a homogeneous mixture, the components will not exhibit phase separation when left at room temperature over a period of 12 hours. This still is a disadvantage in the fact that the materials will eventually phase separate with time. Another distinct disadvantage is that this system is typically cured in a substantially oxygen-free atmosphere or a nitrogen atmosphere. Therefore, handling becomes more complicated and pot-life of the formulated material becomes limited. Lastly, the use of photoinitiators in the UV-curing composition and their potential by-products almost certainly precludes its use in applications such as transdermal drug delivery systems which are loaded with active agents that could react or degrade in such environments.

As alluded to above, there remains a need to improve upon the pressure sensitive adhesives of the prior art to produce a silicone acrylate hybrid composition which has the advantages of both silicone PSAs and acrylic PSAs. A need also exists for such a hybrid composition which demonstrates no gross phase separation for any period of time. A need also exists for a hybrid composition which possesses PSA properties that are alterable over a wide formulation range in order to provide greater flexibility than the compositions of the prior art.

SUMMARY OF THE INVENTION AND ADVANTAGES

A silicone acrylate hybrid composition is disclosed. A method of making the hybrid composition is also disclosed. The hybrid composition includes the reaction product of a silicon-containing pressure sensitive adhesive composition, an ethylenically unsaturated monomer, and an initiator. The silicon-containing pressure sensitive adhesive composition includes acrylate or methacrylate functionality. The method (I) provides the silicon-containing pressure sensitive adhesive composition and (II) polymerizes the ethylenically unsaturated monomer and the silicon-containing pressure sensitive adhesive composition in the presence of the initiator to form the silicone acrylate hybrid composition.

The hybrid composition of the present invention, i.e., the reaction product of the silicon-containing pressure sensitive adhesive composition, the ethylenically unsaturated monomer, and the initiator, is a new and unique polymerized species that is a pressure sensitive adhesive. The polymerization of the ethylenically unsaturated monomer and the silicon-containing pressure sensitive, which already contains acrylate or methacrylate functionality, chemically integrates the advantageous functionalities associated with both acrylic and silicone chemistries into one, stable pressure sensitive adhesive that resists phase separation. Furthermore, during the polymerization of the ethylenically unsaturated monomer and the silicon-containing pressure sensitive adhesive, the silicone to acrylic ratio can be sufficiently controlled and optimized. The ratio of the types of monomers chosen can also be sufficiently controlled and optimized. In transdermal drug delivery system applications, the balance of silicone to acrylic can be selectively used to control solubility of an active agent in the pressure sensitive adhesive, i.e., the hybrid composition, to optimize the rate at which the active agent is released from the system and also the total amount of the active agent that is ultimately released.

DETAILED DESCRIPTION

A silicone acrylate hybrid composition, which is itself a pressure sensitive adhesive (also commonly referred to as a PSA), comprises the reaction product of silicon-containing pressure sensitive adhesive composition, an ethylenically unsaturated monomer, and an initiator. That is, the silicone acrylate hybrid composition is the product of the chemical reaction between these reactants (the silicon-containing pressure sensitive adhesive composition, the ethylenically unsaturated monomer, and the initiator). The term 'pressure sensitive adhesive' and the acronym 'PSA' are used interchangeably throughout the subject description. As just one example, the silicon-containing pressure sensitive adhesive composition may also be referred to as the silicon-containing PSA composition.

The silicone acrylate hybrid composition may be or include the reaction product of silicon-containing pressure sensitive adhesive composition, a (meth)acrylate monomer, and an initiator (i.e., in the presence of the initiator). That is, the silicone acrylate hybrid composition may be the product of the chemical reaction between these reactants (the silicon-containing pressure sensitive adhesive composition, the (meth)acrylate monomer, and the initiator).

The silicone acrylate hybrid composition of the present invention may also be referred to as a silicone acrylic hybrid composition as the terms acrylate and acrylic are generally used interchangeably throughout this description. As used in the description of the present invention, the terms silicone acrylate and silicone acrylic are intended to denote more than a simple blend of a silicone-based sub-species and an acrylate-based sub-species. Instead, these terms denote a polymerized hybrid species that includes silicone-based sub-species and acrylate-based sub-species that have been polymerized together. The ethylenically unsaturated monomer and the initiator introduced above are described additionally below.

The term 'pressure sensitive adhesive' and the acronym 'PSA' are used interchangeably throughout the subject description. As just one example, the silicon-containing pressure sensitive adhesive composition may also be referred to as the silicon-containing PSA composition. The silicon-containing pressure sensitive adhesive composition is typically present in the hybrid composition in an amount of from 5 to 95, more typically 25 to 75, parts by weight based on 100 parts by weight of the hybrid composition.

In one embodiment, the silicon-containing pressure sensitive adhesive composition itself comprises the condensation reaction product of a pressure sensitive adhesive and a silicon-containing capping agent. As also explained additionally below, the silicon-containing capping agent may provide the acrylate or methacrylate functionality to the silicon-containing pressure sensitive adhesive. It is to be understood that, in the context of the description of the present invention, the term 'pressure sensitive adhesive' is distinguishable from the term 'silicon-containing pressure sensitive adhesive composition'. The silicon-containing pressure sensitive adhesive composition, as described above, is typically the reaction product of the pressure sensitive adhesive and a silicon-containing capping agent. That is, the silicon-containing pressure sensitive adhesive composition is essentially a pressure sensitive adhesive that has been capped or endblocked with the capping agent or agents described herein. The capping agent and the pressure sensitive adhesive react to form the composition.

In one embodiment, the pressure sensitive adhesive (before reaction with the capping agent) comprises the condensation reaction product of the silicone resin and the silicone polymer, which may optionally react in the presence of a catalyst, such as a condensation catalyst, e.g. an acid or base catalyst. Alternatively, the capping agent may provide an in-situ catalyst upon reaction, e.g. as HCl generated from chlorosilane. In this embodiment, an independent catalyst may be used or may be omitted. Typically, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive.

Although not required, the pressure sensitive adhesive may comprise a catalytic amount of a condensation catalyst.

There is a wide array of silicone resins and silicone polymers that are suitable to make up the pressure sensitive adhesive. Suitable silicone resins and silicone polymers include, but are not limited to, those disclosed and described in U.S. Pat. No. 6,337,086 to Kanios et al., the disclosure of which is incorporated by reference herein in its entirety.

A preferred silicone resin comprises a copolymer comprising triorganosiloxy units of the formula $R^3{}_3SiO_{1/2}$ and tetrafunctional siloxy units of the formula $SiO_{4/2}$ in a ratio of about 0.6 to 0.9 triorganosiloxy units for each tetrafunctional siloxy unit, wherein each $R^3$ independently denotes a monovalent hydrocarbon radical having from 1 to 6 carbon atoms, and a preferred silicone polymer comprises at least one polydiorganosiloxane comprising $AR^3SiO$ units terminated with endblocking $TR^3ASiO1/2$ units, wherein the polydiorganosiloxane has a viscosity of from about 100 centipoise to about 30,000,000 centipoise at 25° C., each A radical is independently selected from $R^3$ or halohydro-carbon radicals having from 1 to 6 carbon atoms, each T radical is independently selected from the group consisting of $R^3$, OH, H or $OR^4$, and each $R^4$ is independently an alkyl radical having from 1 to 4 carbon atoms.

As an example using forms of this preferred silicone resin and this preferred silicone polymer, one type of pressure sensitive adhesive is made by:

mixing (i) from 30 to 80 inclusive parts by weight of at least one resin copolymer containing silicon-bonded hydroxyl radicals and consisting essentially of $R^3{}_3SiO_{1/2}$ units and $SiO_{4/2}$ units in a mole ratio of 0.6 to 0.9 $R^3{}_3SiO_{1/2}$ units for each $SiO_{4/2}$ unit present, (ii) between about 20 and about 70 parts by weight of at least one polydiorganosiloxane comprising $AR^3SiO$ units terminated with endblocking $TR^3ASiO1/2$ units, wherein the polydiorganosiloxane has a viscosity of from about 100 centipoise to about 30,000,000 centipoise at 25° C. and each $R^3$ is a monovalent organic radical selected from the group consisting of hydrocarbon radicals of from 1 to 6 inclusive carbon atoms, each A radical is independently selected from $R^3$ or halohydrocarbon radicals having from 1 to 6 inclusive carbon atoms, each T radical is independently selected from the group consisting of $R^3$, OH, H or $OR^4$, and each $R^4$ is independently an alkyl radical of from 1 to 4 inclusive carbon atoms; a sufficient amount of (iii) at least one of the silicon-containing capping agents, also referred to throughout as endblocking agents, described below and capable of providing a silanol content, or concentration, in the range of 5,000 to 15,000, more typically 8,000 to 13,000, ppm, when desirable an additional catalytic amount of (iv) a mild silanol condensation catalyst in the event that none is provided by (ii), and when necessary, an effective amount of (v) an organic solvent which is inert with respect to (i), (ii), (iii) and (iv) to reduce the viscosity of a mixture of (i), (ii), (iii), and (iv), and condensing the mixture of (i), (ii), (iii) and (iv) at least until a substantial amount of the silicon-containing capping agent or agents have reacted with the silicon-bonded hydroxyl radicals and T radicals of (i) and (ii). Additional organosilicon endblocking agents can be used in conjunction with the silicon-containing capping agent or agents (iii) of the present invention. Such additional organosilicon endblocking agents, also referred to herein as a second silicon-containing capping agent, are described additionally below.

The pressure sensitive adhesives are made in accordance with the present invention using from 30 to 80 inclusive parts by weight of silicone copolymer resins (i) and from 20 to 70 parts by weight of polydiorganosiloxane (ii) of the type which have been used in the past to make such adhesives. More preferred are compositions employing from 40 to 75 parts by weight of resin copolymer (i) and from 25 to 60 parts by weight of polydiorganosiloxane (ii).

The silicone resin copolymers (i) contain silicon-bonded hydroxyl radicals in amounts which typically range from about 1 to 4 weight percent of silicon-bonded hydroxyl radicals and comprise triorganosiloxy units of the formula $R^3_3SiO_{1/2}$ and tetrafunctional siloxy units of the formula $SiO_{4/2}$ in a mole ratio of from 0.6 to 0.9 $R^3_3SiO_{1/2}$ units for each $SiO_{4/2}$ unit present. Blends of two or more such copolymers may also be used. There should be at least some and typically at least 0.5% silicon-bonded hydroxyl content to enable the polydiorganosiloxane component to copolymerize with the copolymer resin and/or to react with the endblocking agent being added to chemically treat the pressure sensitive adhesive. These resin copolymers are generally benzene-soluble resinous materials which are typically solids at room temperature and are prepared as, and usually, but not necessarily used as, a solution in an organic solvent. Typical organic solvents used to dissolve resin copolymer (i) include benzene, toluene, xylene, methylene chloride, perchloroethylene, naphtha mineral spirits and mixtures of these.

Resin copolymer (i) consists essentially of from 0.6 to 0.9 $R^3_3SiO_{1/2}$ units for every $SiO_{4/2}$ unit in the copolymer. There may also be a few mole percent of $R^3_2SiO$ units present in the copolymer provided that the presence of such units does not cause the ultimate product of this process to lose its ability to function as a PSA. Each $R^3$ denotes, independently, a monovalent hydrocarbon radical having from 1 to 6 inclusive carbon atoms such as methyl, ethyl, propyl, isopropyl, hexyl, hexenyl, cyclohexyl, vinyl, allyl, propenyl and phenyl. Typically, the $R^3_3SiO_{1/2}$ units are $Me_3SiO_{1/2}$ units and/or $Me_2R^1SiO_{1/2}$ units wherein is $R^1$ is a vinyl ("Vi") or phenyl ("Ph") radical. More typically, no more than 10 mole percent of the $R^3_3SiO_{1/2}$ units present in resin copolymer (i) are $Me_2R^2SiO_{1/2}$ units and the remaining units are $Me_3SiO_{1/2}$ units where each $R^2$ is a vinyl radical. Most typically, the $R^3_3SiO_{1/2}$ units are $Me_3SiO_{1/2}$ units.

The mole ratio of $R^3_3SiO_{1/2}$ and $SiO_{4/2}$ units can be determined simply from knowledge of the identity of the $R^3$ radicals in the $R^3_3SiO_{1/2}$ units and the percent carbon analysis of the resin copolymer. In the preferred resin copolymer consisting of from 0.6 to 0.9 $Me_3SiO_{1/2}$ units for every $SiO_{4/2}$ unit, the carbon analysis has a value of from 19.8 to 24.4 percent by weight.

Resin copolymer (i) may be prepared according to Daudt et al., U.S. Pat. No. 2,676,182 (issued Apr. 20, 1954 and hereby incorporated by reference) whereby a silica hydrosol is treated at a low pH with a source of $R^3_3SiO_{1/2}$ units such as a hexaorganodisiloxane such as $Me_3SiOSiMe_3$, $ViMe_2SiOSiMe_2Vi$ or $MeViPhSiOSiPhViMe$ or triorganosilane such as $Me_3SiCl$, $Me_2ViSiCl$ or $MeViPhSiCl$. Such copolymer resins are typically made such that the copolymer resin contains about 1 to 4 weight percent of silicon-bonded hydroxyl radicals. Alternatively, a mixture of suitable hydrolyzable silanes free of $R^3$ radicals may be cohydrolyzed and condensed. In this alternative procedure, it is a typical practice to further treat the copolymer product with a suitable silylating agent, such as hexamethyldisilazane or divinyltetramethyldisilazane, to reduce the silicon-bonded hydroxyl content of the copolymer product to less that 1 percent by weight. This step would not be necessary, but could be used, in the process now being described. Typically, the resin copolymers employed contain from about 1 to 4 weight percent of silicon-bonded hydroxyl radicals.

Ingredient (ii) is one or more polydiorganosiloxanes comprising $AR^3SiO$ units terminated with endblocking $TR^3ASiO1/2$ units, each of which polydiorganosiloxanes has a viscosity of from 100 centipoise to 30,000,000 centipoise at 25° C. (100 millipascal-seconds to 30,000 pascal seconds (Pa·s) where 1 centipoise equals 1 millipascal second). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25° C. range from fluids to somewhat viscous polymers. These polydiorganosiloxanes are typically prereacted with resin copolymer (i) prior to condensation in the presence of endblocking agent (iii) to improve the tack and adhesion properties of the resulting pressure sensitive adhesive as will be further described. Polydiorganosiloxanes having viscosities in excess of 100,000 centipoise can typically be subjected to the condensation/endblocking step without prereaction. Polydiorganosiloxanes having viscosities in excess of 1,000,000 centipoise are highly viscous products often referred to as gums and the viscosity is often expressed in terms of a Williams Plasticity value (polydimethylsiloxane gums of about 10,000,000 centipoise viscosity typically have a Williams Plasticity Value of about 50 mils (1.27 mm) or more at 25° C.).

The polydiorganosiloxanes of (ii) consist essentially of $AR^3SiO$ units where each $R^3$ is as defined above. Each A radical is selected from radicals such as $R^3$ or halohydrocarbon radicals of from 1 to 6 inclusive carbon atoms such a chloromethyl, chloropropyl, 1-chloro-2-methylpropyl, 3,3,3-trifluoropropyl and $F_3C(CH_2)_5$ radicals. Thus, the polydiorganosiloxane can contain $Me_2SiO$ units, $PhMeSiO$ units, $MeViSiO$ units, $Ph_2SiO$ units, methylethylsiloxy units, 3,3,3-trifluoropropyl units and 1-chloro, 2-methylpropyl units and the like. Typically, the $AR^3SiO$ units are selected from the group consisting of $R^3_2SiOR^3R^4SiO$ units, $Ph_2SiO$ units and combinations of both where $R^3$ and $R^4$ are as above, at least 50 mole percent of the $R^4$ radicals present in the polydiorganosiloxane (ii) are methyl radicals and no more than 50 mole percent of the total moles of $AR^3SiO$ units present in each polydiorganosiloxane of (ii) are $Ph_2SiO$ units. More typically, no more than 10 mole percent of the $AR^3SiO$ units present in each polydiorganosiloxane (ii) are $MeR^3SiO$ units where $R^3$ is as above defined and the remaining $AR^3SiO$ units present in each polydiorganosiloxane are $Me_2SiO$ units. Most typically, substantially all of the $AR^3SiO$ units are $Me_2SiO$ units.

Each polydiorganosiloxane (ii) is terminated with endblocking units of the unit formula $TR^3ASiO_{1/2}$ where $R^3$ and A are as defined above and each T radical is $R^3$, OH, H or $OR^4$ radicals where each $R^4$ is an alkyl radical of from 1 to 4 inclusive carbon atoms such as methyl, ethyl, n-propyl, and isobutyl radicals. H, OH and $OR^4$ provide a site for reaction with the acrylate or methacrylate functional silicon-containing capping agent and also provide a site for condensation with other such radicals on polydiorganosiloxanes (ii) or with the silicon-bonded hydroxyl groups present in resin copolymer (i). Use of polydiorganosiloxanes where T is OH is most preferred because the polydiorganosiloxane (ii) can then readily copolymerize with the resin copolymer (i). When an appropriate catalyst such as HCl, which is generated when chlorosilanes are used, or ammonia, which is generated when organosilazanes are used as endblocking agents, then triorganosiloxy (e.g., $R^3_3SiO_{1/2}$ such as $(CH_3)_3SiO_{1/2}$ or $CH_2CH(CH_3)_2SiO_{1/2}$) unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing H, OH or $OR^4$ radicals or silicon-bonded hydroxyl radicals exposed by cleavage reactions. Mixtures of polydiorganosiloxanes containing different substituent radicals may also be used.

Methods for the manufacture of such polydiorganosiloxanes are well known as exemplified by the following U.S. Pat. Nos. 2,490,357 (Hyde); 2,542,334 (Hyde); 2,927,907 (Polmanteer); 3,002,951 (Johannson); 3,161,614 (Brown, et al.); 3,186,967 (Nitzche, et al.); 3,509,191 (Atwell), and 3,697,473 (Polmanteer, et al.) which are hereby incorporated by reference.

To obtain pressure sensitive adhesives which are to be cured by peroxide or through aliphatically unsaturated radicals present in resin copolymer (i) or polydiorganosiloxane (ii), if resin copolymer (i) contains aliphatically unsaturated radicals, then polydiorganosiloxane (ii) should be free of such radicals and vice-versa. If both components contain aliphatically unsaturated radicals, curing through such radicals can result in products which do not act as pressure sensitive adhesives.

As alluded to above, the pressure sensitive adhesive may include a concentration of silicon bonded hydroxyl groups (i.e., silanols) and the silicon-containing capping agent is further defined as an endblocking agent. Once again, the terms endblocking agents and capping agents are used interchangeably throughout the art and in the subject description. The endblocking agent and the pressure sensitive adhesive may be condensed to produce the silicon-containing pressure sensitive adhesive composition. More specifically, the endblocking agent may react with the concentration of silicon bonded hydroxyl groups to cap the pressure sensitive adhesive. As generally alluded to above, once the endblocking agent reacts with the pressure sensitive adhesive, the concentration of silanols in the composition is from 5,000 to 15,000, more typically from 8,000 to 13,000, ppm.

Although not required, the pressure sensitive adhesive is typically present in the silicon-containing pressure sensitive adhesive composition in an amount of from 85.0 to 99.9 parts by weight based on weight % solids of the pressure sensitive adhesive, and the silicon-containing capping agent is typically present in the silicon-containing pressure sensitive adhesive composition in an amount of from 0.1 to 15 parts by weight based on weight % solids of the pressure sensitive adhesive. More typically, the pressure sensitive adhesive is present in the silicon-containing pressure sensitive adhesive composition in an amount of from 90.0 to 99.8 parts by weight based on weight % solids of the pressure sensitive adhesive, and the silicon-containing capping agent is typically present in the silicon-containing pressure sensitive adhesive composition in an amount of from 0.2 to 10 parts by weight based on weight % solids of the pressure sensitive adhesive. Typically, the pressure sensitive adhesive has a weight % solids of from 50 to 65%, more typically 60%.

The endblocking agent can be introduced to react with the pressure sensitive adhesive after the pressure sensitive adhesive has already been formed, i.e., after the silicone resin and the silicone polymer which make up the pressure sensitive adhesive have reacted. In this case, the silicon-containing capping agent reacts with the pressure sensitive adhesive after the silicone resin and the silicone polymer have been condensation reacted to form the pressure sensitive adhesive.

Alternatively, the endblocking agent can be reacted in situ with the silicone resin and/or the silicone polymer such that the endblocking agent is present as the silicone resin and the silicone polymer are reacting. That is, in this in situ scenario, the endblocking agent may be introduced either prior to or during the reaction of the silicone resin and the silicone polymer. In any event, in this in situ scenario, the silicone resin and the silicone polymer are reacted in the presence of the silicon-containing capping agent, and the silicon-containing capping agent is reacted in situ with the silicone resin and the silicone polymer as the silicone resin and the silicone polymer are condensation reacting to form the pressure sensitive adhesive.

The acryl group provides the silicon-containing capping agent with acrylate functionality and the methacryl group provides the silicon-containing capping agent with the methacrylate functionality. Those skilled in the art recognize that the acryl group can be generically represented as

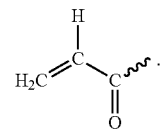

The methacryl group can be generally represented as

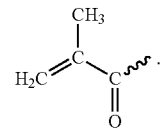

Even further, the endblocking agent may be described to be of the general formula $XYR'_bSiZ_{3-b}$ wherein X is a monovalent radical of the general formula AE- where E is —O— or —NH— and A is an acryl group or a methacryl group as set forth above, Y is a divalent alkylene radical having from 1 to 6 carbon atoms, R' is a methyl or a phenyl radical, Z is a monovalent hydrolyzable organic radical or a halogen, and b is 0 or 1. Typically, the monovalent hydrolyzable organic radical is of the general formula R"O— where R" is an alkylene radical. Most typically, this particular endblocking agent is selected from the group of 3-methacryloxypropyldichlorosilane, 3-methacryloxypropyltrichlorosilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, (methacryloxymethyl)methyldimethoxysilane, (methacryloxymethyl)trimethoxysilane, (methacryloxymethyl)methyldiethoxysilane, methacryloxymethyltriethoxysilane, methacryloxypropyltriisopropoxysilane, 3-acryloxypropyldichlorosilane, 3-acryloxypropyltrichlorosilane, 3-acryloxypropylmethyldimethoxysilane, 3-acryloxypropyltrimethoxysilane, and combinations thereof.

As alluded to above, a second silicon-containing capping agent can be used in conjunction with the silicon-containing capping, or endblocking, agent of the present invention. This second silicon-containing capping agent is distinguishable from the silicon-containing capping agent in that the second silicon-containing capping agent is free of acrylate and methacrylate functionality. If included, the second silicon-containing capping agent, an organosilicon endblocking agent, is along with the silicon-containing capping agent and the pressure sensitive adhesive a reaction product that forms the composition. The second silicon-containing capping agent is capable of generating an endblocking triorganosilyl unit. Suitable second silicon-containing capping agents include, but are not limited to, those described in U.S. Pat. No. 6,337,086 to Kanios et al., the disclosure of which has already been incorporated by reference in its entirety.

As originally described above, the ethylenically unsaturated monomer is a reactant that, along with the silicon-containing pressure sensitive adhesive and the initiator, reacts to form the hybrid composition of the present invention. More specifically, in the method of making the hybrid composition of the present invention, once the silicon-containing pressure sensitive adhesive composition described above is provided, the ethylenically unsaturated monomer and the silicon-containing pressure sensitive adhesive composition are polymerized in the presence of the initiator. Said differently, the method (I) provides the silicon-containing pressure sensitive adhesive composition and (II) polymerizes the ethylenically unsaturated monomer and the silicon-containing pressure sensitive adhesive composition in the presence of the initiator to form the silicone acrylate hybrid composition.

The ethylenically unsaturated monomer is typically present in the hybrid composition in an amount of from 5 to 95, more typically from 25 to 75, parts by weight based on 100 parts by weight of the hybrid composition. Although the present invention is described primarily in the context of one ethylenically unsaturated monomer, it is to be understood that more than one ethylenically unsaturated monomer, i.e., a combination of ethylenically unsaturated monomers, may be polymerized, more specifically co-polymerized, along with the silicon-containing pressure sensitive adhesive and the initiator. Generally, the acrylic portion of the subject hybrid composition, formed via the reaction of the ethylenically unsaturated monomer and the silicon-containing pressure sensitive adhesive, is typically formed similar to acrylate-based PSAs with a combination of monomers that can be broadly described as a main monomer and a modifying monomer as is described extensively in Chapter 19 of the Handbook of Pressure Sensitive Adhesive Technology, Third Edition, Donatas Satas, Satas & Associates, 1999, Warwick, R.I.

The ethylenically unsaturated monomer can be any monomer having at least one carbon-carbon double bond. It is preferred that the ethylenically unsaturated monomer used in the present invention is a compound selected from the group of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms.

The aliphatic acrylates that may be selected as one of the ethylenically unsaturated monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the ethylenically unsaturated monomers are selected from the group consisting of methyl methacrylate, ethyl methacrylate, propyl methacrylate, n-butyl methacrylate, iso-butyl methacrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the ethylenically unsaturated monomers is cyclohexyl acrylate, and the cycloaliphatic methacrylate that may be selected as one of the ethylenically unsaturated monomers is cyclohexyl methacrylate.

Certain other monomers, described herein as polar monomers, may be used as the ethylenically unsaturated monomer and may include supplemental functionality such as hydroxyl functionality. A polar monomer as used herein is an acrylic or methacrylic monomer having at least one polar group such as hydroxyl, alkoxy, amino, and alkenyl heterocycles. Examples of these polar monomers that are useful in the present invention include, but are not limited to, hydrophilic ethylenically unsaturated monomers of an amphoteric, anionic, cationic or anionic nature which are polymerizable by radical polymerization. More specific examples of these polar monomers include, but are not limited to, acrylic acid, methacrylic acid, itaconic acid, vinyl acetic acid, hydroxy ethyl acrylate, hydroxy ethyl methacrylate, hydroxy propyl acrylate, hydroxy propyl methacrylate, methoxyethyl acrylate, methoxyethyl methacrylate, aminoethyl acrylate, aminoethyl methacrylate, 2-N,N,N-trimethylammonium ethyl acrylate, 2-N,N,N-trimethylammonium ethyl methacrylate, acrylonitrile, methacrylonitrile, N,N-dimethylacrylamide, N-t-butylacrylamide, acrylamide, N-vinyl pyrrolidone, 2-acrylamido-2-methyl propane sulphonic acid, or salts thereof and the like.

In one embodiment, the ethylenically unsaturated monomer is further defined as a (meth)acrylate monomer which can be any monomer having at least one acrylate functional group and/or at least one methacrylate functional group. In other words, the terminology "(meth)" describes that the "meth" group is optional and not required. Thus, the monomer may be an acrylate monomer or a methacrylate monomer. It is typical that the (meth)acrylate monomer is a compound selected from the group of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms.

The ethylenically unsaturated monomer and the silicon-containing pressure sensitive adhesive composition are polymerized in the presence of the initiator. It is generally preferred that the polymerization of the ethylenically unsaturated monomer and the silicon-containing pressure sensitive adhesive composition in the presence of the initiator is conducted at a temperature of from 50 to 100° C., more typically of from 65 to 90° C. It is to be understood that the method of the present invention can be employed in a batch process, semi-continuous process, or continuous process. The method of the present invention is also 'flexible' in that the method accounts for rate controlled addition of the ethylenically unsaturated monomer or monomers which also contribute to the ability to control the silicone to acrylic ratio as described below.

Although not required, the silicon-containing pressure sensitive adhesive composition, the ethylenically unsaturated monomer, and the initiator may be mixed to form a pre-reaction mixture prior to the step of (II) polymerizing and this pre-reaction mixture may be combined with a solvent prior to the step of polymerization. If these optional steps are conducted, then the polymerization occurs with the components in the pre-reaction mixture after the pre-reaction mixture has been combined with the solvent.

It is to be understood that there are many different initiation mechanisms contemplated for use in the present invention to initiate the polymerization of the silicon-containing pressure sensitive adhesive composition and the ethylenically unsaturated monomer. However, the preferred initiator is that known throughout the art as a free radical initiator and is detailed in Chapter 3 of Principles of Polymerization, Fourth Edition, George Odian, Wiley-Interscience, 2004, New Jersey. Generally, free radical initiators include peroxides, azo compounds, redox initiators, and photo-initiators. The most preferred free radical initiators for application in the present invention are selected from the group of peroxides, azo compounds, and combinations thereof. The initiator is typically present in the hybrid composition in an amount of from 0.005 to 3, more typically from 0.01 to 2, parts by weight based on 100 parts by weight of the hybrid composition. Notably, once the hybrid composition is formed, peroxides can serve additional functions in the context of the present invention not relating to initiation. Specifically, peroxides can function has cross-linking agents as described additionally below.

For descriptive purposes only, a generic representation is included below to generally illustrate the polymerization of the silicon-containing pressure sensitive and the ethylenically unsaturated monomer in the presence of the initiator to make the inventive hybrid composition.

all acrylic content. In other applications, it may be desirable for the opposite to be true. Independent of the end application, it is generally preferred, as already described above, that the silicon-containing pressure sensitive adhesive composition is typically present in the hybrid composition in an amount of from 5 to 95, more typically from 25 to 75, parts by weight based on 100 parts by weight of the hybrid composition.

Typically, a solvent is used during the polymerization to make the hybrid composition to decrease the viscosity of the reaction mixture which allows for adequate mixing and heat transfer. The solvent may be any suitable material which is inert to the reaction ingredients and does not interfere with the reaction itself. Suitable solvents include, but are not limited to, aliphatic hydrocarbons such as hexane and heptane; alcohols such as methanol, ethanol and butanol; ketones such as acetone, methyl ethyl ketone and methyl isobutyl ketone; esters such as ethyl acetate, n-butyl acetate and i-butyl acetate; low viscosity silicone oils with linear, cyclic or branched structures which have a boiling point below 250° C. and a viscosity below 100 centistokes such as octamethylcyclotetrasiloxane, decamethylcyclopentasiloxane and hexamethyldisiloxane; and mixtures of two or more of the above mentioned solvents. If utilized, the amount of solvent is typi-

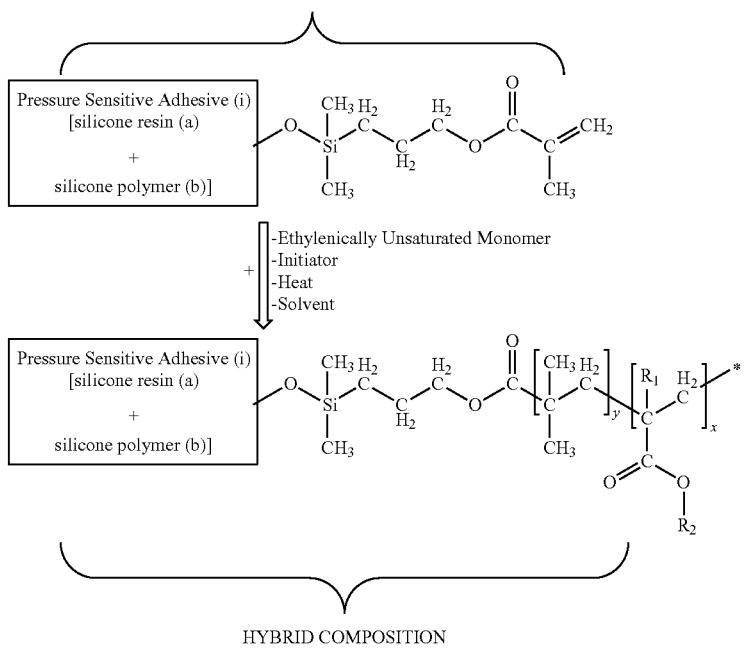

During the polymerization of the ethylenically unsaturated monomer and the silicon-containing pressure sensitive adhesive, the silicone to acrylic ratio can be sufficiently controlled and optimized as desired. Controlling the silicone to acrylic ratio is desirable because the hybrid composition can be optimized dependent on the end application for the hybrid composition. The silicone to acrylic ratio can be controlled by a wide variety of mechanisms in and during the method. An illustrative example of one such mechanism is the rate controlled addition of the ethylenically unsaturated monomer or monomers to the silicon-containing pressure sensitive adhesive composition. In certain applications, it may be desirable to have the silicone-based sub-species, or the overall silicone content, to exceed the acrylate-based sub-species, or the overcally present in an amount of from 30 to 95, more typically 40 to 70, parts by weight based on the total amount of the reactants and solvent.

For cases where the molecular weight of the polymerization is to be controlled or limited, a chain transfer agent may be used. Chain transfer agents are known in the art and can include mercaptans, such as 1-butanethiol and dodecanethiol. If utilized, the amount of the chain transfer agent is typically from about 0 to 0.5 parts by weight per 100 parts by weight of the hybrid composition.

The hybrid compositions described herein can be used as prepared to prepare PSA films for use as tapes or transdermal drug delivery systems in accordance with well-known coating, or application, techniques. Optionally, when an application requires higher shear strength (i.e., cohesive strength) than is afforded by the neat hybrid composition, the crosslink density of the film resulting from the hybrid composition can be increased in accordance with well-known procedures for both pure acrylate-based PSAs and pure silicone-based PSAs, which are described in Chapters 19 and 21, respectively, of the Handbook of Pressure Sensitive Adhesive Technology, Third Edition, Donatas Satas, Satas & Associates, 1999, Warwick, R.I.

When using the crosslinking techniques known for traditional acrylate PSAs for the hybrid compositions of the present invention, it is important to ensure that an amount of hydroxy or carboxylic functional monomer is incorporated into the initial polymerization steps for the hybrid composition. The amount of this functional monomer should be present from 0.5 to 20 parts by weight based on total amount of monomer. If, for example, functional groups resulting from the incorporation of these functional monomers are available in the hybrid composition, then the crosslink density is when various metal acetyl acetonates and orthoalkyl titanates are added prior to casting, i.e., coating. As is understood in the art, crosslink density is an indicator of static shear and cohesive strength. Such metal acetyl acetonates and orthoalkyl titanates are often referred to in the art as cross-linking agents. One specific suitable example of such a cross-linking agent is aluminum acetyl acetonate (AlAcAc). AlAcAc is used below in Example 29.

If the technique for curing, i.e., cross-linking, traditional silicone PSAs is used for the hybrid compositions of the present invention to improve static shear, then about 0.25 to 3.0% by weight of a peroxide cross-linking agent, such as dibenzoyl peroxide (BPO) or 2,4-dichlorobenzoylperoxide, based on the non-volatile content of the hybrid composition, can be added to the hybrid composition prior to casting. Once casted, the film can be cured at 110° C. to 175° C. for 1 to 10 minutes. As is known in the art, the peroxide cross-linking agent effectively extracts hydrogen off of one chain of the hybrid composition and another hydrogen off of another chain of the hybrid composition, and these two chains will then chemically react. One specific suitable example of a peroxide cross-linking agent is BPO. BPO is used below in Example 30.

The silicone acrylate hybrid composition of the present invention can also be strategically blended with other non-hybrid pressure sensitive adhesive compositions known in the art including, but not limited to, other silicone pressure sensitive adhesive compositions, acrylic pressure sensitive adhesive compositions, polyurethane pressure sensitive adhesive compositions, natural rubber pressure sensitive adhesive compositions, synthetic rubber pressure sensitive adhesive compositions, and blends, e.g. physical blends, thereof. One such blend is a blend of acrylic and rubber pressure sensitive adhesive compositions. Examples of these non-hybrid type pressure sensitive adhesive compositions and of blending are disclosed in U.S. Pat. Nos. 5,474,783; 5,656,286; 6,024,976; 6,221,383; 6,235,306; 6,465,004; 6,638,528; 5,464,659; and 5,624,763, the disclosures of which are hereby incorporated by reference in their entirety.

In many of the applications described in the present invention, including tapes, labels and transdermal drug delivery systems, it is often necessary to use a backing layer and a release layer. The backing layer can be any of the typical substrates used for tapes such as those selected from polymeric films (e.g. polyethylene, polyester, polyimide, polyolefins, polypropylene, polyurethane, PTFE, etc.), metal foils, glass cloth, PTFE-coated glass cloth, paper (e.g. crepe, super-calendared craft, etc.), cloth, nonwoven materials, foams (e.g. polyurethane, acrylate, silicone, neoprene, etc.) and rubbers (e.g. silicone, butyl, etc.). Release liners are generally supplied on a backing such as paper or film and are applied to the hybrid composition after the drying and/or curing steps are complete. Three general types of release coatings the are suitable for use with both silicone-based PSAs and acrylate-based PSAs, and also with the hybrid composition of the present invention are known in the art and are commercially available: silicone-based release liners (e.g. Dow Corning® Syl-off™ 7680), perfluoropolyether-based release liners (e.g. 3M SCOTCH-PAK® 1022 Release Liner) and fluorosilicone-based release liners (e.g. Dow Corning® Syl-off™ Q2-7785). The release liner for a particular application will be dependant upon the ratio of silicone-to-acrylate in the hybrid composition. For a hybrid composition that contains a low level of silicon-containing PSA as compared to the ethylenically unsaturated monomer (e.g. 20 parts silicon-containing PSA and 80 parts ethylenically unsaturated monomer), a silicone-based release liner can be used. If the hybrid composition contains a high level of silicone-containing PSA as compared to the ethylenically unsaturated monomer (e.g. 80 parts silicon-containing PSA and 20 parts ethylenically unsaturated monomer), then either a perfluoropolyether-based or fluorosilicone-based liner should be chosen.

One particularly important application for the hybrid composition of the present invention is in a transdermal drug delivery system. The system includes an active agent and the hybrid composition of the present invention functioning as a pressure sensitive adhesive. The active agent and its relationship to the hybrid composition in the context of the system are described in detail below. As those skilled in the art appreciate, the system is structural and can be in many forms including, but not limited to, patches, films, multi-layer dressings, reservoir systems, and combinations thereof. The active agent is in the system for controlled transdermal delivery to a substrate. It is also possible, but not required, for the system to include a backing layer for supporting the hybrid composition, and/or a release liner for protecting the hybrid composition and/or the active agent prior to the controlled transdermal delivery of the active agent to the substrate. One preferred application of the transdermal drug delivery system of the present invention is to treat a user, or patient, with the active agent. As a result, the substrate is typically the skin of the user and, in this preferred application, the user applies and wears the system on their skin.

The active agent can be any component suitable for transdermal delivery to a substrate. Suitable active agents include, but are not limited to, those active agents disclosed and described in U.S. Pat. No. 5,474,783 to Miranda et al., the disclosure of which is incorporated by reference herein in its entirety. These active agents include, but are not limited to, cardioactive medications, androgenic steroids, estrogens, hormones, progestational agents, drugs having an action on the central nervous system, nutritional agents, anti-inflammatory agents, antihistamines, respiratory agents, sympathomimetics, miotics, cholinergic agonists, antimuscarinic or muscarinic cholinergic blocking agents, mydriatics, psychicenergizers, anti-infectives, dermatological agents, humoral agents, antispasmodics, antidepressant drugs, anti-diabetic, anorectic drugs, anti-allergenics, tranquilizers, antipsychotics, decongestants, antipyretics, antimigrane agents, drugs for treating nausea and vomiting, anti-malarials, anti-ulcerative agents, peptides, drugs for Parkinson's disease, drugs for spasticity, drugs for acute muscle spasms, anti-estrogen, anti-hormone agents, therapeutic agents, and combinations thereof.

More specific examples of the active agents outlined above that are suitable for implementation as the active agent in the present invention include:

Cardioactive medications, illustratively, organic nitrates such as nitroglycerin, isosorbide dinitrate and, isosorbide mononitrates; quinidine sulfate; procainamide; thiazides such as bendroflumethiazide, chlorothiazide, and hydrochlorothyazide; nifedipine; nicardipine; adrenergic blocking agents, such as timolol, and propranolol; verapamil; diltiazem; captopril; clonidine and prazosin;

Androgenic steroids, such as testosterone, methyltestosterone and fluoxymesterone;

Estrogens, such as, conjugated estrogens, esterified estrogens, quinestrol, estropipate, 17-β estradiol, 17-β estradiol valerate, equilin, mestranol, estrone, estriol, 17-β ethinyl estradiol, and diethylstilbestrol;

Progestational agents, such as progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-alpha-hydroxyprogesterone, dydrogesterone, dimethisterone, ethinylestrenol, norgestrel, demegestone, promegestone, and megestrol acetate;

Drugs having an action on the central nervous system, for example sedatives, hyponotics, antianxiety agents, analgesics and anesthetics, such as chloral, buprenorphine, naloxone, haloperidol, fluphenazine, pentobarbital, phenobarbital, secobarbital, codeine, lidocaine, tetracaine, dyclonine, dibucaine, cocaine, procaine, mepivacaine, bupivacaine, etidocaine, prilocalne, benzocaine, fentanyl, and nicotine;

Nutritional agents, such as vitamins (e.g. niacinamide), essential amino acids and essential fats;

Anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprofen, naproxen, fenoprofen, fenbufen, flurbiprofen, acetaminophen, indoprofen, ketoprofen, suprofen, indomethacin, piroxicam, aspirin, salicylic acid, diflunisal, methyl salicylate, phenylbutazone, sulindac, mefenamic acid, meclofenamate sodium, naproxen, and the like;

External analgesics, such as camphor, menthol, capsicum extract, frankincense, green tea, juniper tea, and caffeine;

Antihistamines, such as diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, terrenadine, and chlorpheniramine;

Respiratory agents, such as theophylline and Beta-adrenergic agonists such as albuterol, terbutaline, metaproterenol, ritodrine, carbuterol, fenoterol, quinterenol, rimiterol, solmefamol, soterenol, and tretoquinol;

Sympathomimetics such as dopamine, norepinephrine, phenylpropanolamine, phenylephrine, pseudoephedrine, amphetamine, propylhexedrine and epinephrine;

Miotics such as pilocarpine, and the like;

Cholinergic agonists, such as choline, acetylcholine, methacholine, carbachol, bethanechol, pilocarpine, muscarine, and arecoline;

Antimuscarinic or muscarinic cholinergic blocking agents, such as atropine, scopolamine, homatropine, methscopolamine, homatropine methylbromide, methantheline, cyclopentolate, tropicamide, propantheline, anisotropine, dicyclomine, and eucatropine;

Mydriatics, such as atropine, cyclopentolate, homatropine, scopolamine, tropicamide, eucatropine and hydroxyamphetamine;

Psychicenergizers, such as 3-(2-aminopropy)indole, 3-(2-aminobutyl)indole, and the like;

Anti-infectives, such as antibiotics, including penicillin, tetracycline, chloramphenicol, sulfacetamide, sulfadiazine, sulfamethoxazole and sulfisoxazole; antivirals, including idoxuridine; antibacterials, such as erythromycin and clarithromycin; anti-fungals, such as ketoconazole, and other anti-infectives including nitrofurazone, cyclopirox, terbafine, witch hazel, and the like;

Dermatological agents, such as retinoids; vitamins C and E; benzoyl peroxide (BPO) (also commonly referred to as dibenzoyl peroxide) and dapsone;

Humoral agents, such as the prostaglandins, natural and synthetic, for example PGE1, PGE 2-alpha, and PGF 2-alpha, and the PGE1 analog misoprostol;

Antispasmodics, such as atropine, methantheline, papaverine, cinnamedrine, and methscopolamine;

Antidepressant drugs, such as paroxetine, phenelzine, tranylcypromine, imipramine, amitriptyline, trimipramine, doxepin, desipramine, nortriptyline, protriptyline, amoxapine, maprotiline, and trazodone;

Anti-diabetics, such as insulin, and anticancer drugs such as tamoxifen and methotrexate;

Anorectic drugs, such as, dextroamphetamine, methamphetamine, phenylpropanolamine, fenfluramine, diethylpropion, mazindol, and phentermine.

Anti-allergenics, such as antazoline, methapyrilene, chlorpheniramine, pyrilamine and pheniramine;

Tranquilizers, such as reserpine, chlorpromazine, and antianxiety benzodiazepines such as alprazolam, chlordiazepoxide, clorazeptate, halazepam, oxazepam, prazepam, clonazepam, flurazepam, triazolam, lorazepam and diazepam;

Antipsychotics, such as thiopropazate, chlorpromazine, triflupromazine, mesoridazine, piperacetazine, thioridazine, acetophenazine, fluphenazine, perphenazine, trifluoperazine, chlorprothixene, thiothixene, haloperidol, bromperidol, loxapine, and molindone;

Decongestants, such as phenylephrine, ephedrine, naphazoline, tetrahydrozoline;

Antipyretics, such as aspirin, salicylamide, and the like;

Antimigrane agents, such as dihydroergotamine and pizotyline;

Drugs for treating nausea and vomiting, such as chlorpromazine, perphenazine, prochlorperazine, promethazine, triethylperazine, triflupromazine, and trimeprazine;

Anti-malarials, such as the 4-aminoquinolines, alphaminoquinolines, chloroquine, and pyrimethamine;

Anti-ulcerative agents, such as misoprostol, omeprazole, and enprostil;

Peptides, such as growth releasing factor;

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, and dantrolene; and Anti-estrogen or hormone agents, such as tamoxifen or human chorionic gonadotropin.

In one embodiment, the active agent is selected from the group of ketoprofen, estradiol, clonidine, and combinations thereof.

As indicated above, the particular active agent is not limited to those recited above. Other examples of suitable active agents for use in the systems will be apparent to those skilled in the art (See, for example, pages 149-217 of Yie Chien's treatise entitled "*Novel Drug Delivery Systems*" which is Volume 14 of *Drugs and the Pharmaceutical Sciences*, Marcel Dekker, Inc., New York, N.Y. 10016 (1982)).

As those skilled in the art appreciate, the active agents can be present in the system in different forms, depending on which form yields optimum delivery characteristic, such as the release rate and the total amount released as described below. For example, in the case of drugs, the drug can be in its free base or acid form, or in the form of salts, esters, or any other pharmacologically acceptable derivatives, or even as components of molecular complexes.

The amount of the active agent incorporated into the system varies depending on many factors including, but not limited to, the particular active agent, the desired therapeutic effect, and the time span for which the system is to provide therapy. For most active agents, the passage of the active agent through the skin is the rate-limiting step in transdermal delivery. Thus, the amount of the active agent and the rate of release are typically selected so as to provide transdermal delivery characterized by a zero order time dependency for a prolonged period of time. The minimum amount of active agent in the system is selected based on the amount of active agent which passes through the skin, or other substrate, in the time span for which the system is to provide therapy. Typically, the amount of active agent in the system varies from about 0.1% up to about 60% by weight of the system, more typically from about 0.3% up to about 50% by weight of the system, and for the lower drug doses permitted by this invention, most typically from about 1.0% up to about 30% by weight of the system. The weight of the system is, at a minimum, the combined weight of the active agent and the hybrid composition. Specific examples of these weight % ranges for the amount of active agent in the system are provided immediately below in the context of three preferred active agents, specifically 17-β estradiol, niacinamide, and ketoconazole.

When the active agent comprises 17-β estradiol, the 17-β estradiol is typically present in an amount of 1.5 to 2.5, 4 to 6, or 7 to 13, parts by weight based on 100 parts by weight of the system depending on the particular drug dosage desired. 2, 5, or 10 parts by weight on this same basis are more preferred values for the 17-β estradiol as the active agent.

When the active agent comprises niacinamide, the niacinamide is typically present in an amount of 1.5 to 2.5, 4 to 6, or 7 to 13, parts by weight based on 100 parts by weight of the system depending on the particular drug dosage desired. 2, 5, or 10 parts by weight on this same basis are more preferred values for the niacinamide as the active agent.

When the active agent comprises ketoconazole, the ketoconazole is typically present in an amount of 1.5 to 2.5, 4 to 6, or 7 to 13, parts by weight based on 100 parts by weight of the system depending on the particular drug dosage desired. 2, 5, or 10 parts by weight on this same basis are more preferred values for the ketoconazole as the active agent.

The aforementioned weight percentages are not limiting and the weight percentage of any one or more active agents may be selected by one of skill in the art. Additional typical, but non-limiting weight percentages of various active agents, are from about 0.1 to about 20, from about 1 to about 10, from about 2 to about 8, from about 3 to about 9, from about 4 to about 6, or about 5, parts by weight per 100 parts by weight of the formulation.

Furthermore, relative to the active agent, it is to be recognized that the active agent is most typically disposed in the hybrid composition. However, it is also to be understood that the active agent and the hybrid composition may coexist in the system in discrete layers. That is, in certain embodiments, the active agent is not disposed, or directly incorporated, into the hybrid composition.

Of course, the transdermal drug delivery system can also contain other agents known to accelerate the delivery of the active agent through the skin or other substrate. These other agents are also referred to in the art as skin-penetration or permeation enhancers, accelerants, adjuvants, and sorption promoters, and are collectively referred herein simply as "enhancers". These enhancers includes those with diverse mechanisms of action including those which have the function of improving the solubility and diffusibility of the active agent within the hybrid composition and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these enhancers have more than one mechanism of action, but in essence they serve to enhance the delivery of the active agent to the substrate.

Some examples of enhancers are polyhydric alcohols such as dipropylene glycol, propylene glycol, and polyethylene glycol which enhance solubility of the active agent, oils such as olive oil, squalene, and lanolin; fatty ethers such as cetyl ether and oleyl ether; fatty acid esters such as isopropyl myristate which enhance diffusibility of the active agent; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the substrate, e.g. skin, and the active agents administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In certain embodiments of the invention, a plasticizer or tackifying agent may be incorporated into the system, typically into the composition, to improve the adhesive characteristics of the hybrid composition. A tackifying agent is particularly useful in those embodiments in which the active agent does not plasticize the silicone polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. The tackifying agent employed is typically compatible with the other components in the composition. Examples of suitable tackifying agents are silicone fluids (e.g., Q7-9120 Silicone Fluid, available from Dow Corning Corporation, Midland, Mich.), silicone resins (e.g., Q2-7466 INT, available from Dow Corning Corporation, Midland, Mich.), or mineral oil. Silicone fluids and silicone resins are useful for blends comprising polysiloxane as a major component. In other embodiments, where a synthetic rubber, for example, is a major component, mineral oil is a useful tackifying agent.

Notably some active agents, such as vasodilator nitroglycerin, function as plasticizers in the composition because they are soluble to a certain degree in the components of the composition. For active agents which are not readily soluble in the components, a co-solvent for the active agent and other components can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the active agent in the composition.

Independent of, or in conjunction with, the tackifying agent, the hybrid composition maintains contact between the system and the substrate. The hybrid composition, also referred to throughout simply as the composition, is an adhesive that possesses sufficient tack and cohesive strength so that it can be adhered with mild pressure and also removed and the adhered again (to the same or another).

In addition to the above described plasticizers and tackifying agents, the hybrid composition may include a variety of other formulation additives that are known in the art. These additives are typically included in small amounts to influence a select physical property or to improve a certain performance feature of the hybrid composition. Examples of these additives include, but are not limited to, fillers, such as silicas or calcium carbonate, pigments, antioxidant agents, defoaming agents, wetting agents, and viscosity adjusting agents. These additives are applicable whether the hybrid composition of the present invention is being used in a transdermal drug delivery system or not.

Aside from the transdermal drug delivery system described above which uses the hybrid composition, there is a wide array of advantages associated with this hybrid composition in a wide variety of applications that is not found by using solely a silicone-based PSA or an acrylate-based PSA. Some of the advantages include, but are not limited to, effective adherence to substrates with a broad range of surface energies, improved solubility of a broader range of drugs, a larger effective temperature use range as compared to a pure acrylate-based PSA, and lower potential cost when compared to a pure silicone-based PSA.

Other applications for the hybrid composition include, but are not limited to, tapes, labels, notes, bandages, transdermal drug delivery systems (e.g. patches), lipstick, hair spray, hair fixatives, and other cosmetic products, transfer adhesives, laminating adhesives, surface priming, and vibration damping.

Several features of the present invention including, but not limited to, the pressure sensitive adhesive (i), the silicon-containing capping agent (ii), the second silicon-containing capping agent, and the features of the transdermal drug delivery system are also described in U.S. Provisional Patent Application Ser. No. 60/730,070, which was filed on Oct. 25, 2005, and PCT International Application No. PCT/US2006/041430, which was filed on Oct. 24, 2006, both of which are entitled "TRANSDERMAL DRUG DELIVERY SYSTEM WITH ACRYLATE OR METHACRYLATE FUNCTIONAL PRESSURE SENSITIVE ADHESIVE COMPOSITION" and the disclosures of which are both hereby incorporated by reference in their entirety. In one or more non-limiting embodiments, one or more components, compounds, etc. that are described in U.S. Ser. No. 13/278,979, filed on Oct. 21, 2011, which is expressly incorporated herein by reference, may also be utilized in this invention.

EXAMPLES

The following Examples illustrating specifics associated with the making of the silicon-containing pressure sensitive adhesive composition and, ultimately, the silicone acrylate hybrid composition of the present invention, as presented herein, are intended to illustrate and not limit the invention.

The components used in the following examples are as follows.

CA 1 is a silicon-containing capping agent which provides the acrylate or methacrylate functionality to the silicon-containing pressure sensitive adhesive composition and is, more specifically, 3-methacryloxypropylmethyldichlorosilane commercially available from Gelest.

CA 2 is a silicon-containing capping agent which provides the acrylate or methacrylate functionality to the silicon-containing pressure sensitive adhesive composition and is, more specifically, 3-methacryloxypropyltrichlorosilane commercially available from Gelest.

CA 3 is a silicon-containing capping agent which provides the acrylate or methacrylate functionality to the silicon-containing pressure sensitive adhesive composition and is, more specifically, 3-methacryloxypropyldimethoxysilane commercially available from Dow Corning.

2-EHA is an ethylenically unsaturated monomer, specifically 2-ethylhexyl acrylate commercially available from Aldrich.

MA is an ethylenically unsaturated monomer, specifically methyl acrylate commercially available from Aldrich.

Vazo® 67 is a free radical initiator, specifically 2,2'-azobis (methylbutyronitrile) commercially available from DuPont.

AIBN is a free radical initiator, specifically 2,2'-azobis (isobutyronitrile) commercially available from Aldrich.

Resin 1 is a 71.79% weight solids solution in xylene comprising trimethylsiloxy and hydroxy end-blocked silicate resin in a three dimensional structure.

Polymer 1 is a hydroxy end-blocked polydimethylsiloxane with a viscosity of 50,000 cp at 25° C. and non-volatile content minimum of 99%.

In the following Examples, all parts and percentages are on a by weight basis, unless otherwise indicated. After formation, some of the Examples are allowed to stand at room temperature and periodically visually evaluated to determine if phase separation occurs.

Comparative Example 1, also referred to below as PSA 1, is a conventional, i.e., uncapped, silicone PSA that is produced through a condensation reaction of a silanol end-blocked polydimethylsiloxane (PDMS) with a silicate resin and is 60% weight solids in ethyl acetate.

Example 1

Dichloro-Functional Capping Agent (Z=2)

To a 32 ounce jar, 811.0 g of PSA 1 and 4.8 g of CA 1 are added. The generation of HCl is immediate as indicated by pH paper color change. The material is allowed to mix overnight on a mixing wheel. The next day 100 g of sodium bicarbonate is added to the material to aid in the neutralization of the HCl. Then the material is allowed to mix overnight. The material is then pressure filtered the next day to remove particulate. The resulting non-volatile content for the material is 60.56%.

Example 2

Trichloro-Functional Capping Agent (Z=3)

To a 32 ounce jar, 831.0 g of PSA 1 and 5.0 g of CA 2 are added. The generation of HCl is immediate as indicated by pH paper color change. The material is allowed to mix overnight on a mixing wheel. The next day, 100 g of sodium bicarbonate is added to the material to aid in the neutralization of the HCl.

The material is allowed to mix overnight. The material is then pressure filtered the next day to remove particulate. The resulting non-volatile content for the material is 62.12%.

Example 3

Using Dichloro-Functional Capping Agent (Z=2) of Example 1

To a 16 ounce jar, 44.5 g of 2-EHA, 19.4 g of MA, 104.5 g of Example 1, 10.5 g of ethyl acetate solvent and 0.091 g of Vazo® 67 are added to form a pre-reaction mixture. The materials in this pre-reaction mixture are allowed to stir 15 minutes until thoroughly homogeneous. After mixing, 42.3 g of the pre-reaction mixture and 123.6 g of ethyl acetate solvent are added to a 4-neck glass reactor equipped with a heating mantle, stifling blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapsed, the mixture in the reservoir is then added at a rate of 0.76 grams/minutes for 180 minutes using a metering pump until the mixture in the reservoir is finished. The mixture in the reactor is then reacted at 78° C. for an additional 480 minutes to form the silicone acrylate hybrid composition. Upon completion, the hybrid composition is allowed to cool to room temperature before removal from the reactor. The final product is opaque. After 2-months of standing at room temperature, this Example does not exhibit phase separation.

Example 4

Using the Trichloro-Functional Capping Agent (Z=3) of Example 2

To a 16 ounce jar, 44.1 g of 2-EHA, 19.1 g of MA, 103.1 g of Example 2, 11.5 g of ethyl acetate solvent and 0.091 g of Vazo® 67 are added to form a pre-reaction mixture. The materials in this pre-reaction mixture are allowed to stir 15 minutes until thoroughly homogeneous. After mixing, 43.6 g of the pre-reaction mixture and 123.8 g of ethyl acetate solvent are added to a 4-neck glass reactor equipped with a heating mantle, stifling blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapsed, the mixture in the reservoir is then added at a rate of 0.79 grams/minutes for 170 minutes using a metering pump until the mixture in the reservoir is finished. The mixture in the reactor is then reacted at 78° C. for an additional 500 minutes to form the silicone acrylate hybrid composition. Upon completion, the hybrid composition is allowed to cool to room temperature before removal from the reactor. The final product is opaque. After 2-months of standing at room temperature, this Example does not exhibit phase separation.

Example 5 (Comparative)

To a 16 ounce jar, 59.1 g of 2-EHA, 25.2 g of MA, 140.1 g of PSA 1, 12.0 g of ethyl acetate solvent, 12.8 g of CA 3 and 0.123 g of Vazo® 67 are added to form a pre-reaction mixture. The materials in this pre-reaction mixture are allowed to stir 15 minutes until thoroughly homogeneous. After mixing, 60.6 g of the pre-reaction mixture and 169.9 g of ethyl acetate solvent are added to a 4-neck glass reactor equipped with a heating mantle, stifling blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 67 minutes prior to adding more of the pre-reaction mixture to the reactor. Once 67 minutes elapsed, the mixture in the reservoir is then added at a rate of 1.00 grams/minutes for 189 minutes using a metering pump until the mixture in the reservoir is finished. The mixture in the reactor is then reacted at 78° C. for an additional 469 minutes to form the silicone acrylate hybrid composition. Upon completion, the hybrid composition is allowed to cool to room temperature before removal from the reactor. The final product is opaque. In this example, the trimethoxy-functional capping agent is added directly in the polymerization step rather than pre-capping. After 2-months of standing at room temperature, this Example exhibits phase separation.

Example 6

Trimethoxy-Functional Capping Agent (Z=3)

273.05 g of Resin 1, 160.38 g of Polymer 1, 3.60 g of CA 3 and 162.97 g of xylene are blended together to yield a nominal 60% solids mixture. The mixture is placed into a glass reactor. The reactor is equipped with a bottom discharge, thermometer, nitrogen inlet, Dean-Starke trap, water-cooled condenser, a stifling paddle and a heating mantle. Under mixing and a nitrogen purge, the reactor is heated to 142° C. A condensation catalyst, anhydrous ammonia, is bubbled through the reaction mixture. As the mixture started to condense, water is collected as an azeotrope in the Dean-Starke trap. The reaction is continued for 4 hours at which time the addition of ammonia is discontinued. The mixture is allowed to continue to reflux for 30 minutes to remove any residual ammonia. The refluxing is complete when the pH of the mixture is neutral. At that time, the heat is discontinued and the mixture, now a PSA composition itself, is allowed to cool to less than 50° C. The mixture is then removed from the reactor. The resulting non-volatile content for the material is 59.92%.

Example 7

Using the Trimethoxy-Functional Capping Agent (Z=3) of Example 6

To a 16 ounce jar, 94.57 g of 2-EHA, 31.52 g of MA, 211.98 g of Example 6 and 0.185 g AIBN are added to form a pre-reaction mixture. The materials in this pre-reaction mixture are allowed to stir 15 minutes until thoroughly homogeneous. After mixing, 95.90 g of the pre-reaction mixture and 189.31 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 30 minutes prior to adding more of the pre-reaction mixture to the reactor. Once 30 minutes elapsed, the mixture in the reservoir is then added at a rate of 1.10 grams/minutes for 220 minutes using a metering pump until the mixture in the reservoir is finished. The mixture in the reactor is then reacted at 78° C. for an additional 105 minutes to form the silicone acrylate hybrid composition. Upon completion, the hybrid composition is allowed to cool to room temperature and then 82.99 grams of ethyl acetate is added to further adjust the solids content of the material. The final product is removed from the reactor and is opaque in color. After 3 years of standing at room temperature, this Example exhibits no phase separation.

These Examples demonstrate that the silicone acrylate hybrid composition of this invention is stable and resists phase separation over time. This stability and resistance to phase separation is notable when compared to Comparative Example 5.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A silicone acrylate hybrid composition that is blended with a non-hybrid pressure sensitive adhesive composition, said silicone acrylate hybrid composition comprising the reaction product of:
    A. a silicon-containing pressure sensitive adhesive composition comprising acrylate or methacrylate functionality and the condensation reaction product of:
    a silicone resin,
    a silicone polymer, and
    a silicon-containing capping agent which provides said acrylate or methacrylate functionality, wherein said silicon-containing capping agent is of the general formula XYR'$_b$SiZ$_{3-b}$ wherein
        X is a monovalent radical of the general formula AE— where E is —O— or —NH— and A is an acryl group or a methacryl group,
        Y is a divalent alkylene radical having from 1 to 6 carbon atoms,
        R' is a methyl or a phenyl radical,
        Z is a monovalent hydrolyzable organic radical or a halogen, and
        b is 0 or 1;
    wherein the silicone resin and silicone polymer are reacted to form a pressure sensitive adhesive, wherein the silicon-containing capping agent is introduced prior to, during, or after the silicone resin and silicone polymer are reacted, and wherein:
        the silicon-containing capping agent reacts with the pressure sensitive adhesive after the silicone resin and silicone polymer have been condensation reacted to form the pressure sensitive adhesive; or
        the silicon-containing capping agent reacts in-situ with the silicone resin and silicone polymer;
    B. an ethylenically unsaturated monomer; and
    C. an initiator.

2. A hybrid composition as set forth in claim 1 wherein said ethylenically unsaturated monomer (B) is a compound selected from the group of aliphatic acrylates, aliphatic methacrylates, cycloaliphatic acrylates, cycloaliphatic methacrylates, and combinations thereof, each of said compounds having up to 20 carbon atoms in the alkyl radical.

3. A hybrid composition as set forth in claim 2 wherein said aliphatic acrylates are selected from the group of methyl acrylate, ethyl acrylate, propyl acrylate, n-butyl acrylate, isobutyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and combinations thereof, and said aliphatic methacrylates are selected from the group of methyl methacrylate, ethyl methacrylate, propyl methacrylate, n-butyl methacrylate, isobutyl methacrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, and combinations thereof.

4. A hybrid composition as set forth in claim 1 wherein said silicon-containing pressure sensitive adhesive composition (A) is present in said hybrid composition in an amount of from 5 to 95 parts by weight based on 100 parts by weight of said hybrid composition.

5. A hybrid composition as set forth in claim 1 wherein said ethylenically unsaturated monomer (B) is present in said hybrid composition in an amount of from 5 to 95 parts by weight based on 100 parts by weight of said hybrid composition.

6. A hybrid composition as set forth in claim 1 wherein said initiator (C) is present in said hybrid composition in an amount of from 0.005 to 3 parts by weight based on 100 parts by weight of said hybrid composition.

7. A hybrid composition as set forth in claim 1 wherein said silicon-containing capping agent is an acrylate functional silane.

8. A hybrid composition as set forth in claim 1 wherein said silicon-containing capping agent is selected from the group of 3-methacryloxypropyldichlorosilane, 3-methacryloxypropyltrichlorosilane, 3-methacryloxypropyldimethoxysilane, 3-methacryloxypropyltrimethoxysilane, 3-methacryloxypropylmethyldiethoxysilane, 3-methacryloxypropyltriethoxysilane, (methacryloxymethyl)methyldimethoxysilane, methacryloxymethyl)trimethoxysilane, (methacryloxymethyl)methyldiethoxysilane, methacryloxymethyltriethoxysilane, methacryloxypropyltriisopropoxysilane, 3-acryloxypropyldichloro silane, 3-acryloxypropyltrichlorosilane, 3-acryloxypropylmethyldimethoxysilane, 3-acryloxypropyltrimethoxysilane, and combinations thereof.

9. A hybrid composition as set forth in claim 1 wherein
    said silicone resin comprises a copolymer comprising triorganosiloxy units of the formula $R^3{}_3SiO_{1/2}$ and tetrafunctional siloxy units of the formula $SiO_{4/2}$ in a ratio of about 0.6 to 0.9 triorganosiloxy units for each tetrafunctional siloxy unit, wherein each $R^3$ independently denotes a monovalent hydrocarbon radical having from 1 to 6 carbon atoms; and
    said silicone polymer comprises at least one polydiorganosiloxane comprising $AR^3SiO$ units terminated with endblocking $TR^3ASiO1/2$ units, wherein the polydiorganosiloxane has a viscosity of from about 100 centipoise to about 30,000,000 centipoise at 25° C., each A radical is independently selected from $R^3$ or halohydrocarbon radicals having from 1 to 6 carbon atoms, each T radical is independently selected from the group consisting of $R^3$, OH, H or $OR^4$, and each $R^4$ is independently an alkyl radical having from 1 to 4 carbon atoms.

10. A hybrid composition as set forth in claim 9 wherein said silicone resin reacts in an amount of from 30 to 80 parts by weight to form said pressure sensitive adhesive (i), and said silicone polymer reacts in an amount of from 20 to 70 parts by weight to form said pressure sensitive adhesive (i), both based on 100 parts by weight of said pressure sensitive adhesive (i).

11. A hybrid composition as set forth in claim 1 wherein said non-hybrid pressure sensitive adhesive composition is selected from the group of silicone pressure sensitive adhesive compositions, acrylic pressure sensitive adhesive compositions, polyurethane pressure sensitive adhesive compositions, natural rubber pressure sensitive adhesive compositions, synthetic rubber pressure sensitive adhesive compositions, and blends thereof.

12. A method of making a silicone acrylate hybrid composition comprising the steps of:
(I) providing a silicon-containing pressure sensitive adhesive composition comprising acrylate or methacrylate functionality and the condensation reaction product of:
a silicone resin,
a silicone polymer, and
a silicon-containing capping agent which provides said acrylate or methacrylate functionality, wherein said silicon-containing capping agent is of the general formula $XYR'_b SiZ_{3-b}$ wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure sensitive adhesive, wherein the silicon-containing capping agent is introduced prior to, during, or after the silicone resin and silicone polymer are reacted, and wherein:
the silicon-containing capping agent reacts with the pressure sensitive adhesive after the silicone resin and silicone polymer have been condensation reacted to form the pressure sensitive adhesive; or
the silicon-containing capping agent reacts in-situ with the silicone resin and silicone polymer; and
(II) polymerizing an ethylenically unsaturated monomer and the silicon-containing pressure sensitive adhesive composition of Step (I) in the presence of an initiator at a temperature of from 50 to 100° C. to form the silicone acrylate hybrid composition.

13. A method of making a hybrid composition as set forth in claim 12 further comprising the step of mixing the silicon-containing pressure sensitive adhesive composition of Step (I), the ethylenically unsaturated monomer of Step (II), and the initiator to form a pre-reaction mixture prior to Step (II).

14. A method of making a hybrid composition as set forth in claim 12 further comprising the step of blending the silicon-containing pressure sensitive adhesive composition with a non-hybrid pressure sensitive adhesive composition.

15. A silicone acrylate hybrid composition comprising the reaction product of:
A. a silicon-containing pressure sensitive adhesive composition comprising acrylate or methacrylate functionality and the condensation reaction product of:
a silicone resin,
a silicone polymer, and
a silicon-containing capping agent which provides said acrylate or methacrylate functionality, wherein said silicon-containing capping agent is of the general formula $XYR'_b SiZ_{3-b}$ wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure sensitive adhesive, wherein the silicon-containing capping agent is introduced prior to, during, or after the silicone resin and silicone polymer are reacted, and wherein:
the silicon-containing capping agent reacts with the pressure sensitive adhesive after the silicone resin and silicone polymer have been condensation reacted to form the pressure sensitive adhesive; or
the silicon-containing capping agent reacts in-situ with the silicone resin and silicone polymer;
B. an ethylenically unsaturated monomer; and
C. a free radical initiator selected from the group of peroxides, azo compounds, and combinations thereof, and
wherein said silicon-containing pressure sensitive adhesive composition is blended with a non-hybrid pressure sensitive adhesive composition.

16. A method of making a silicone acrylate hybrid composition comprising the steps of:
(I) providing a silicon-containing pressure sensitive adhesive composition comprising acrylate or methacrylate functionality and the condensation reaction product of:
a silicone resin,
a silicone polymer, and
a silicon-containing capping agent which provides said acrylate or methacrylate functionality, wherein said silicon-containing capping agent is of the general formula $XYR'_b SiZ_{3-b}$ wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure sensitive adhesive, wherein the silicon-containing capping agent is introduced prior to, during, or after the silicone resin and silicone polymer are reacted, and wherein:
the silicon-containing capping agent reacts with the pressure sensitive adhesive after the silicone resin and silicone polymer have been condensation reacted to form the pressure sensitive adhesive; or the silicon-containing capping agent reacts in-situ with the silicone resin and silicone polymer; and (II) polymerizing an ethylenically unsaturated monomer and the silicon-containing pressure sensitive adhesive composition of Step (I) in the presence of a free radical initiator at a temperature of from 50 to 100° C. to form the silicone acrylate hybrid composition, wherein the free radical initiator is selected from the group of peroxides, azo compounds, and combinations thereof.

17. A method of making a hybrid composition as set forth in claim 16 further comprising the step of blending the silicon-containing pressure sensitive adhesive composition with a non-hybrid pressure sensitive adhesive composition.

18. A transdermal drug delivery system comprising:
I. an active agent for controlled transdermal delivery to a substrate; and
II. a silicone acrylate hybrid composition for maintaining contact with the substrate, said hybrid composition comprising acrylate or methacrylate functionality and the condensation reaction product of:
a silicone resin,
a silicone polymer, and
a silicon-containing capping agent which provides said acrylate or methacrylate functionality, wherein said silicon-containing capping agent is of the general formula $XYR'_b SiZ_{3-b}$ wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure sensitive adhesive, wherein the silicon-containing capping agent is introduced prior to, during, or after the silicone resin and silicone polymer are reacted, and wherein:
the silicon-containing capping agent reacts with the pressure sensitive adhesive after the silicone resin and silicone polymer have been condensation reacted to form the pressure sensitive adhesive; or
the silicon-containing capping agent reacts in-situ with the silicone resin and silicone polymer;
an ethylenically unsaturated monomer; and
a free radical initiator selected from the group of peroxides, azo compounds, and combinations thereof,
wherein said silicone acrylate hybrid composition is blended with a non-hybrid pressure sensitive adhesive composition.

19. A system as set forth in claim 18 wherein said active agent is selected from the group of cardioactive medications, androgenic steroids, estrogens, hormones, external analgesics, progestational agents, drugs having an action on the central nervous system, nutritional agents, anti-inflammatory agents, antihistamines, respiratory agents, sympathomimetics, miotics, cholinergic agonists, antimuscarinic or muscarinic cholinergic blocking agents, mydriatics, psychicenergizers, anti-infectives, dermatological agents, humoral agents, antispasmodics, antidepressant drugs, anti-diabetic, anorectic drugs, anti-allergenics, tranquilizers, antipsychotics, decongestants, antipyretics, antimigrane agents, drugs for treating nausea and vomiting, anti-malarials, anti-ulcerative agents, peptides, drugs for Parkinson's disease, drugs for spasticity, drugs for acute muscle spasms, anti-estrogen, anti-hormone agents, therapeutic agents, and combinations thereof.

20. A system as set forth in claim 19 wherein said active agent is disposed in said hybrid composition for the controlled transdermal delivery to the substrate.

21. A system as set forth in claim 19 wherein said active agent and said hybrid composition coexist in said system in discrete layers.

22. A system as set forth in claim 19 further comprising;
a backing layer for supporting said hybrid composition; and/or
a release liner for protecting said hybrid composition and/ or said active agent prior to the controlled transdermal delivery to a substrate.

23. A system as set forth in claim 19 selected from the group of patches, films, multi-layer dressings, reservoir systems, and combinations thereof.

* * * * *